United States Patent [19]

Hjorth

[11] Patent Number: 5,718,904
[45] Date of Patent: Feb. 17, 1998

[54] ADJUVANTS FOR VIRAL VACCINES

[75] Inventor: Richard N. Hjorth, King of Prussia, Pa.

[73] Assignee: American Home Products Corporation, Madison, N.J.

[21] Appl. No.: 459,600

[22] Filed: Jun. 2, 1995

[51] Int. Cl.$^6$ .......... A61K 45/00; A61K 45/05; A61K 39/21; A61K 47/00

[52] U.S. Cl. .......... 424/278.1; 424/281.1; 424/188.1

[58] Field of Search .......... 424/278.1, 281.1, 424/188.1

[56] References Cited

U.S. PATENT DOCUMENTS

| | | | |
|---|---|---|---|
| 4,073,743 | 2/1978 | Midler et al. | 424/85 |
| 4,466,957 | 8/1984 | Hjorth et al. | 424/278.1 |
| 5,376,369 | 12/1994 | Allison et al. | 424/88 |

OTHER PUBLICATIONS

Bull. Org. Mond. Sante/Bull. Wld. Hlth. Org., 41, 617–621, 1969.
The Lancet, vol. 344, Jul. 16, 1994, 160–163.
Vaccine, vol. 11, Issue 3, 1993, 293–306.
Journal of Clinical Microbiology, vol. 13, No. 1, 54–57, Jan. 1981.
Infection and Immunity, vol. 28, No. 3, 937–943, 1980.
Proc. Natl. Acad. Sci., vol. 89, 8308–8312, 1992.
Vaccines, vol. 11, Issue 13, 1302–1309, 1993.
Bio/Technology, vol. 5, Oct. 1987.
Vaccines 92, Copyright 1992.
Vaccines, Plenum Press, New York, 1991.
Vaccines, vol. 11, 9, 909–913, 1993.

*Primary Examiner*—Lynette F. Smith
*Attorney, Agent, or Firm*—Steven R. Eck

[57] ABSTRACT

The present invention discloses mammalian vaccine compositions having an effective amount of an adjuvant, the adjuvant comprising squalene or squlane, glycerol and a surfactant. These compositions also optionally contain an aluminum salt and one or more pharmaceutically acceptable buffers.

10 Claims, No Drawings

ADJUVANTS FOR VIRAL VACCINES

This invention relates to new adjuvants that are useful in increasing the antigenicity of mammalian vaccines. More particularly, this invention relates to new adjuvants which utilize squalene or squalane, or mixtures thereof, glycerol and a surfactant.

BACKGROUND OF THE INVENTION

Four major categories of vaccines are used to raise antibodies to disease in mammals, particularly in humans. These are living vaccines, killed or inactivated vaccines, subunit vaccines and toxoids. Of this group, living vaccines produce the strongest immune response in the host. These living vaccines are generally attenuated such that they are able to mount a lengthy immune response to their antigens without producing the disease with which they are normally associated.

Killed vaccines are inactivated by chemical or other means which do not inactivate the antigenic factors which they present to the host's immune system. The pertussis and Salk poliomyelitis vaccines are examples of killed vaccines.

For some disease vectors, even killing the organism does not prevent it from causing undesired effects in the recipient. In such cases, the agent must be fragmented into subunits or subfractions which are not, by themselves, pathogenic. Examples of such subunit vaccines include some influenza vaccines and some experimental herpes virus and hepatitis vaccines.

Finally, toxoid vaccines are those in which a toxin excreted by an organism is rendered nontoxic and then used just as any other antigenic factor to stimulate an immune response to the toxin. Tetanus toxoid is an example of such a vaccine.

Unfortunately, the subunit and toxoid vaccines rarely furnish enough antigens to trigger a long-lasting immunity in the host. Therefore, the immunity induced by the nonliving vaccines, and especially the highly purified subunit vaccines, lasts only for one to two years.

Various adjuvants have been described to strengthen the immunogenicity of nonliving vaccines. Among them is Freund's complete adjuvant, which comprises mineral oil, water, and emulsifier and killed tuberculosis bacteria. Of the many adjuvants available for use in mammals, only a few, including aluminum hydroxide and aluminum phosphate, have been widely used in humans. Several adjuvants have been rejected for use in humans because they cause severe local or systematic reactions. Some of them, such as Freund's complete adjuvant which contains mineral oil, are non-metabolizable and by causing cancer in laboratory animals are seen as potentially carcinogenic. There exists, therefore, a need for effective and safe adjuvants which can enhance the action of vaccines, expecially the subunit type vaccines which are currently available and those which may be developed.

DESCRIPTION OF THE INVENTION

The present invention is directed to mammalian vaccine compositions comprising an inactivated whole or subunit vaccine or toxoid and an adjuvant.

The adjuvant of this invention comprises a mixture of squalene, glycerol and surfactant. More particularly, this first adjuvant comprises a mixture of these components with a mammalian vaccine in which squalene comprises from about 1% to about 40% of the total mixture, glycerol comprises from about 5% to about 40% of the total mixture, and surfactant comprises from about 0.1% to about 4.0% of the total mixture. The percentages listed herein indicate the percent by volume of each component and it will be understood that the remaining percentage of the total mixture is generated by the vaccine, itself, or by the vaccine and the optional aluminum salts and buffers described herein.

In a more preferred aspect of this invention, the adjuvant's squalene component comprises from about 2% to about 20% of the total mixture, glycerol comprises from about 10% to about 30% of the total mixture, and surfactant comprises from about 0.15% to about 1.6% of the total mixture. In a still more preferred aspect of this invention, the adjuvant's squalene component comprises from about 3% to about 7% of the total mixture, the glycerol component comprises from about 15% to about 25% of the total mixture, and the surfactant component comprises from about 0.18 % to about 0.22% of the total mixture.

By the term Squalene is indicated the compound described on page 1383 of the Merck Index, 11th Edition, as (all-E)-2, 6, 10, 15, 19, 23-Hexamethyl-2, 6,-10, 14, 18, 22-tetracosahexaene, as well as by the names Sinacene and Supraene. Squalane, also referred to on page 1383 of the Merck Index, 11 th Edition, as 2,6,10,15,19,23-Hexamethyltetracosane; perhydrosqualene; dodecahydrosqualene; and spinacane, can be used in place of, or in mixtures with, the Squalene component of the adjuvant mixtures described herein.

Surfactants that may be used with the present formulations include, but are not limited to, Polysorbate 20 (polyoxyethylene 20 sorbitan monolaurate), Polysorbate 60, Span 80® Sorbitan Oleate, a product of ICI Americas, Wilmington, Del., the Cremophor® surfactants produced by the BASF Corporation, Parsippany, N.J., and Polysorbate 80, which is known as Sorbitan mono-9-octadecenoate poly(oxy-1,2-ethanediyl) derivatives, polyoxyethylene (20) sorbitan mono-oleate, Sorbitan mono-oleate polyoxyethylene, Sorlate, Tween 80, among others, and indicates an oleate ester of sorbitol and its anhydrides copolymerized with approximately 20 moles of ethylene oxide for each mole of sorbitol and sorbitol anhydrides. Polysorbate 80 is the surfactant preferred for use with the present invention.

The glycerol component of these adjuvants will be understood by those skilled in the art to refer to the commercially available alcohol also known as 1,2,3-Propanetriol; glycerin; glycerine; or trihydroxypropane.

Optionally, the adjuvants of this invention also contain one or more pharmaceutically acceptable aluminum salts, such as aluminum hydroxide, aluminum phosphate or aluminum sulphate, at a weight/volume concentration of from about 0.1% to about 2.0%, preferably from about 0.3% to about 0.7%, most preferably about 0.5%. Aluminum hydroxide is the preferred aluminum salt.

The adjuvants of this invention may also optionally contain one or more of the pharmaceutically acceptable pH buffers, such as phosphate buffered saline (PBS), Tris-HCl, citrate-phosphate buffer, Tricine buffer, Hepes and maleate buffers. Other salts, such as KCl, can be substituted for the sodium chloride in the PBS buffer if the final solution is maintained at a substantially isotonic condition. These buffers are preferably used to maintain the adjuvant mixture at a pH of between 6.0 and 8.0.

The adjuvants of this invention are preferably made with sterile components or made sterile through known thermal or filtration means. The adjuvant mixture may be stored at 4°

C. If the adjuvant is not sterile, storage at 4° C. for more than 3 days is not recommended. Stock solutions of microfluidized, sonicated or homogenized adjuvants of this invention can be stored frozen at a temperature preferably of −20° C. or lower.

The adjuvants used in the composition of this invention exhibit a marked immunomodulatory activity and it is postulated that the adjuvanting effect of these compounds is a direct result of their ability to modulate the immune response. Moreover, because the components of these adjuvants lack reactogenic potential, their suitability for use as adjuvants for vaccines is even further enhanced. It should also be noted that these adjuvants are comprised of known injectable materials and are seen in commercially available injectables.

The vaccines used in the composition of the invention can be administered in any manner prescribed for the particular vaccine utilized, preferably via intramuscular or subcutaneous injections. They can be used in either veterinary or human vaccines, and include both inactivated whole and subunit vaccines as well as toxoids. Moreover, the vaccines employed are those used to immunize against bacterial, rickettsial and viral pathogens. Suitable human vaccines would include for example, the whole and subunit vaccines for influenza, poliomyelites, arbovirsus infections, typhoid and paratyphoid, ekolcra, plague, pertussis, typhus, Rocky Mountain Spotted Fever, Haemophilus influenza type B, multivalent pneumococcal polysaccharid, meningococcal group C and the newly developed human diploid cell rabies vaccines and hepatitus vaccine.

Suitable veterinary vaccines would include, for example, the whole and subunit vaccines for equine influenza viruses, equine herpesviruses, equine encephalomyelitis viruses, wart virus, foot-and-mouth disease virus, rabies, feline panleukopenia, feline rhinotracheitis, feline calicivirus, infectious bovine rhinotracheitis, parainfluenza-3, bovine virus diarrhea, bovine adenoviruses, pseudorabies, transmissible gastroenteritis virus, porcine parvovirus, canine adenoviruses, canine distemper virus and canine parainfluenza. Whole and subunit vaccines, bacterins and toxoids for strangles, brucellosis, vibriosis, leptospirosis, clostridial infections, salmonellosis, colibacillosis, anaplasmosis, pasteurella infections, haemophilus infections, erysipelothrix and the like. Further, it is fully contemplated that since the vaccines of the future, especially the vital and bacterial subunit types, may likely be weak immunogens, they will require potentiation via a suitable and acceptable adjuvant, and it is felt that the system of the present invention will be highly suitable.

The advantages of using the disclosed potent adjuvants with vaccines are significant. By modulating certain compartments of the immune system, the adjuvants can cause an increase in the immune reactivity of the humoral immunity, resulting in a potentiated antibody production to the antigenic material contained in the vaccine preparation with which the adjuvants are administered to the recipient. Such potentiation, of course, will permit stronger and longer levels of immunity to be achieved, even though the immunizing agent may be a weak immunogen, such as may be found with many of the inactivated whole and especially the subunit vaccines and toxoids. This potentiation of immune response to antigen has a direct result of this effect, the futher advantage that it is possible to use less immunizing antigenie, material thereby decreasing the potential for serious and stressful host reactions to the immunization. This is particularly important in the vaccinations of juveniles. Moreover, in addition to making immunizations more successful and safer with a reduced dose of purified antigen, vaccine production can be made more economical and more feasible.

The compositions of the invention are prepared by dissolving or suspending the adjuvant material in the antigen diluent and then combining suitable volumes of the adjuvant solution and the antigen solution at the appropriate antigen dilution. The antigen diluents are those conventional in the art, such as phosphate buffered saline, minimum essential medium, peptone and the like.

Adjuvants of this invention may be mixed together at greater than their final concentration and later diluted with vaccine and, optionally, buffer prior to use or storage. It is preferable that sterile adjuvant components are used or, in some cases, that sterile filtration is used. The resulting combination of adjuvant components is then thoroughly homogenized, preferably with a homogenizer at an appropriate rate and time to insure homogenization of the mixture, for example at a time of from about 1 to about 10 minutes, prior to being mixed with the vaccine of choice.

More particularly, the adjuvants of this invention may be produced by the following steps:

1) All adjuvant components should first be brought to a temperature of about 37° C.

2) The buffer, if used, squalene component and the glycerol component should be mixed together and be allowed to come to room temperature. This mixture should be held at room temperature for about 15 minutes.

3) The surfactant component is then added to the mixture, with mixing. This total mixture of adjuvant components can then be autoclaved and sonicated to create a sterile, homogenous adjuvant mixture. Sonication may be completed with a Heat Systems probe type sonicator at a setting of about No. 6 in an ice bath. A total sonication time of at least five minutes is recommended, with the time being divided into sonication pulses of approximately 30 seconds followed by 15 seconds gaps of holding the adjuvant mixture on ice. As a more consistent and preferred alternative to this type of sonication, the adjuvant mixture may be microfluidized or homogenized until it passes through a 0.22 µm filter. If desired, the aluminum salts described herein may then be added to the adjuvant composition with mixing.

4) Vital vaccines or vaccine concentrates can then be added to the adjuvant mixture according to the desired dose.

5) The adjuvant/vaccine combination can then be gently mixed. An additional amount of buffer may be added during mixing to bring the final mixture to a desired volume.

EXAMPLE 1

Adjuvants of this invention and comparative adjuvants were prepared and mixed with trivalent Wyeth-Ayerst 1993 influenza virus vaccine, which is described on page 2578 of the 1993 Physician's Desk Reference, 47th Edition. 1.5 µg of the hemagglutinin of each of the three strains present in the vaccine, A/Beijing/32/92, A/Texas/36/91 and B/Panama/45/90, were given to groups of 6 female, 7-week old CD-1 mice. Each mouse received intramuscular injections of 0.2 ml of the Wyeth-Ayerst vaccine. At 28 days following innoculation, the mice were bled and the serum assayed by the hemagglutination inhibition procedure for antibodies to the A/Beijing component. The Table I, below, lists the results for each expressed as the geometric mean tiler of the 6 mice in each group. It should be noted that PBS buffer was used qs to bring the adjuvants and comparative adjuvants described herein to the desired volume.

The adjuvants used were the following:

Adjuvant No. 1) an adjuvant mixture containing 5% squalene, 5% glycerol and 0.2% Tween 80.

Comparative Adjuvant No. 1) The vehicle for Syntex Adjuvant Formulation-Microfluidized, as used by Syntex Laboratories. This adjuvant comprised 5% squalene, 1.25% Pluronic L-121 (which is commercially available from BASF Wyandotte Corp.) and 0.2% Tween 80.

Comparative Adjuvant No. 2) a 5% squalene/0.2% Tween 80 adjuvant mixture.

Comparative Adjuvant No. 3) a 5% squalene/1.0% Tween 80 adjuvant mixture.

Comparative Adjuvant No. 4) a 5% squalene/2.0% Tween 80 adjuvant mixture.

Comparative Adjuvant No. 5) a 5% squalene/4.0% Tween 80 adjuvant mixture.

Comparative Adjuvant No. 6) a 5% squalene, 0.2% Lecithin, 0.2% Tween 80 adjuvant mixture.

Comparative Adjuvant No. 7) a 5% squalene, 5% Glycerol, 0.5% Lecithin adjuvant mixture.

Comparative Adjuvant No. 8) a 5% squalene, 0.2% Povidone, 0.2% Tween adjuvant mixture.

Comparative Adjuvant No. 9) the vaccine in PBS buffer, alone.

TABLE I

| Influenza Adjuvants | |
|---|---|
| Adjuvant | HI Titer (Thousands) |
| Adjuvant No. 1 | 2.048 |
| Comp. Adj. No. 1 | 5.793 |
| Comp. Adj. No. 2 | 1.825 |
| Comp. Adj. No. 3 | 1.625 |
| Comp. Adj. No. 4 | 2.048 |
| Comp. Adj. No. 5 | 2.048 |
| Comp. Adj. No. 6 | 1.29 |
| Comp. Adj. No. 7 | 1.149 |
| Comp. Adj. No. 8 | 0.406 |
| Comp. Adj. No. 9 | 0.406 |

EXAMPLE 2

Additional adjuvant testing was completed with groups of Cynomolgus monkeys. Each group of 3 monkeys was inoculated intramuscularly with 0.5 ml of trivalent Wyeth-Ayerst 1993 influenza virus vaccine (as described on page 2578 of the 1993 Physician's Desk Reference, 471h Edition) mixed 50:50 with the adjuvants described below. On day 28 following the initial vaccination, the monkeys were boosted with the same inoculum. 5 ml of blood were drawn from each monkey at day 28 and day 42 for creatinine phosphokinase (cpk) analysis, the results of which are shown for each group of three monkeys in Table II, below. As mentioned above, PBS buffer was used qs to bring the adjuvant/vaccine combinations described below to their desired volume.

Adjuvant Mixtures Tested

Adjuvant A: An adjuvant mixture of this invention comprising 5% squalene, 20% glycerol and 0.2% Tween 80.

Comparative Adjuvant A: A vaccine mixture containing only vaccine in PBS buffer.

Comparative Adjuvant B: An adjuvant mixture comprising 2 mg cholesterol hemisuccinate (CHS) or cholesteryl hydrogen succinate liposomes, which are commercially available from Sigma Chemical Company, St. Louis, Mo., catalog no. C 6013.

Comparative Adjuvant C: An adjuvant mixture containing 5% Squalene, 30% Propylene Glycol and 0.2% Tween 80.

TABLE II

| Adjuvants in Cynomolgus Monkeys HI Titer vs A/Beijing (GMT) | | |
|---|---|---|
| Adjuvant | Day 28 | Day 42 |
| Adjuvant A | 203 | 645 |
| Comp. Adj. A | 8 | 8 |
| Comp. Adj. B | 51 | 102 |
| Comp. Adj. C | 102 | 256 |

What is claimed:

1. A mammalian vaccine composition of an inactivated whole or subunit vaccine and an effective amount of an adjuvant, the adjuvant consisting essentially of squalene in the amount of from about 1% to about 40% by volume of the total composition, glycerol in the amount of from about 5% to about 40% by volume of the total composition, and a surfactant in the amount of from about 0.1% to about 4.0% of the total composition.

2. The mammalian vaccine composition of claim 1 in which the adjuvant consists essentially of squalene in the amount of from about 2% to about 20% by volume of the total composition, glycerol in the amount of from about 10% to about 30% by volume of the total composition, and a surfactant in the amount of from about 0.15% to about 1.6% of the total composition.

3. The mammalian vaccine composition of claim 1 in which the adjuvant consists essentially of squalene in the amount of from about 3% to about 7% by volume of the total composition, glycerol in the amount of from about 15% to about 25% by volume of the total composition, and a surfactant in the mount of from about 0.18% to about 0.22% of the total composition.

4. The mammalian vaccine composition of claim 1 further containing a pharmaceutically acceptable pH buffer.

5. The mammalian vaccine of claim 4 in which the pharmaceutically acceptable pH buffer is PBS.

6. The mammalian vaccine composition of claim 1 in which the vaccine is a subunit influenza A vaccine.

7. The mammalian vaccine composition of claim 1 in which the squalene is replaced by an equivalent mount of squalane.

8. The mammalian vaccine composition of claim 1 in which the squalene is replaced by an equivalent amount of a mixture of squalene and squalane.

9. A mammalian vaccine composition of an inactivated whole or subunit vaccine and an effective amount of an adjuvant in a pharmaceutically acceptable buffer, the adjuvant consisting essentially of squalene in the mount of from about 3% to about 7% by volume of the total composition, glycerol in the amount of from about 15% to about 25% by volume of the total composition, a surfactant in the mount of from about 0.18% to about 0.22% of the total composition and from about 0.1% weight/volume to about 2.0% weight/volume of an aluminum salt.

10. The mammalian vaccine composition of claim 9 in which the aluminum salt is aluminum hydroxide.

* * * * *